United States Patent
Yang et al.

(10) Patent No.: US 10,406,602 B2
(45) Date of Patent: Sep. 10, 2019

(54) METHODS TO PRODUCE ULTRA-THIN METAL NANOWIRES FOR TRANSPARENT CONDUCTORS

(71) Applicant: The Regents of the University of California, Oakland, CA (US)

(72) Inventors: Peidong Yang, Kensington, CA (US); Jianwei Sun, Albany, CA (US); Yi Yu, Berkeley, CA (US); Fan Cui, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 64 days.

(21) Appl. No.: 15/513,023

(22) PCT Filed: Sep. 25, 2015

(86) PCT No.: PCT/US2015/052180
§ 371 (c)(1),
(2) Date: Mar. 21, 2017

(87) PCT Pub. No.: WO2016/049430
PCT Pub. Date: Mar. 31, 2016

(65) Prior Publication Data
US 2018/0326498 A1 Nov. 15, 2018

Related U.S. Application Data

(60) Provisional application No. 62/056,338, filed on Sep. 26, 2014.

(51) Int. Cl.
| | | |
|---|---|---|
| *B22F 9/24* | (2006.01) |
| *B22F 1/00* | (2006.01) |
| *C07F 1/08* | (2006.01) |
| *C07F 7/08* | (2006.01) |
| *C07F 7/12* | (2006.01) |
| *B82B 3/00* | (2006.01) |
| *H01B 1/02* | (2006.01) |
| *C07F 7/18* | (2006.01) |
| *H01B 13/00* | (2006.01) |
| *B82Y 30/00* | (2011.01) |
| *B82Y 40/00* | (2011.01) |

(52) U.S. Cl.
CPC ............. *B22F 9/24* (2013.01); *B22F 1/0025* (2013.01); *B82B 3/00* (2013.01); *C07F 1/08* (2013.01); *C07F 7/0896* (2013.01); *C07F 7/12* (2013.01); *C07F 7/1804* (2013.01); *H01B 1/02* (2013.01); *H01B 13/0016* (2013.01); *H01B 13/0036* (2013.01); *B22F 2301/10* (2013.01); *B82Y 30/00* (2013.01); *B82Y 40/00* (2013.01)

(58) Field of Classification Search
CPC ...... B22F 9/24; B22F 1/0025; B22F 2301/10; H01B 1/02; H01B 13/0016; H01B 13/0036; B82Y 30/00; B82Y 40/00
USPC .......................................... 428/402
See application file for complete search history.

(56) References Cited

U.S. PATENT DOCUMENTS

2013/0230717 A1* 9/2013 Xia ................. B22F 1/0025
428/397

FOREIGN PATENT DOCUMENTS

| | | | |
|---|---|---|---|
| JP | 2009-035781 A | | 2/2009 |
| JP | 2009035781 | * | 2/2009 |
| JP | 2013-147713 A | | 8/2013 |
| JP | 2013147713 | * | 8/2013 |
| KR | 2010-0079781 A | | 7/2010 |
| KR | 20100079781 | * | 7/2010 |

OTHER PUBLICATIONS

Nickitas-Etienne, Athina, International Preliminary Report on Patentability and Written Opinion, PCT/US2015/052180, The International Bureau of WIPO, dated Apr. 6, 2017.
Lange, Tim, International Search Report and Written Opinion, PCT/US2015/052180, dated Feb. 18, 2016.

* cited by examiner

*Primary Examiner* — Leszek B Kiliman
(74) *Attorney, Agent, or Firm* — Gavrilovich, Dodd & Lindsey LLP (57) ABSTRACT

The disclosure provides methods to produce ultrathin metal nanowires, the metal nanowires produced therefrom, and the use of the metal nanowires as transparent conductors.

24 Claims, 6 Drawing Sheets

METHODS TO PRODUCE ULTRA-THIN METAL NANOWIRES FOR TRANSPARENT CONDUCTORS

CROSS REFERENCE TO RELATED APPLICATIONS

This application is a U.S. National Stage Application filed under 35 U.S.C. § 371 and claims priority to International Application No. PCT/US2015/052180, filed Sep. 25, 2015, which application claims priority under 35 U.S.C. § 119 from Provisional Application Ser. No. 62/056,338, filed Sep. 26, 2014, the disclosures of which are incorporated herein by reference.

TECHNICAL FIELD

The disclosure provides methods to produce ultrathin metal nanowires, the ultrathin metal nanowires made therefrom, and their use as transparent conductors.

BACKGROUND

Transparent conducting electrodes are an essential component of numerous optoelectronic devices, like touch panels, display electrodes (LCD & OLED), photovoltaic devices, and electrochromic windows. As such, the demand for transparent conducting electrodes is growing exponentially, giving rise to a huge market.

SUMMARY

The disclosure provides innovative synthesis methods to produce uniform, ultrathin and high-quality metal nanostructures. In certain embodiments, the synthesis methods disclosed herein are solution based, therefore affording scalability and allowing for the production of metal nanostructures (e.g., Cu-nanowires) that can have varying diameters, e.g., between 1 nm to 70 nm. The resulting metal nanostructures can be used to construct transparent electrodes that have lower costs, better transparency, and superior flexibility in comparison to conventional metal-oxide conductors, such as indium tin oxide (ITO). The resulting metal nanowire transparent electrodes can be utilized in numerous optoelectronic devices, like touch panels, display electrodes (LCD & OLED), photovoltaic devices, and electrochromic windows.

In a certain embodiment, the disclosure provides a method to synthesize an ultrathin copper elongated nanostructure. The method includes forming a reaction mixture comprising a silane-based reducing agent, a copper metal salt and a surface ligand, wherein the surface ligand may also be a solvent; and heating and maintaining the reaction mixture at an elevated temperature between 1 to 48 hours with or without stirring. In one embodiment, the copper metal salt is selected from CuI, CuBr, CuCl, CuF, CuSCN, $CuCl_2$, $CuBr_2$, $CuF_2$, $CuOH_2$, Cu-D-gluconate, $CuMoO_4$, $Cu(NO_3)_2$, $Cu(ClO_4)_2$, $CuP_2O_7$, $CuSeO_3$, $CuSO_4$, Cu-tartrate, $Cu(BF_4)_2$, $Cu(NH_3)_4SO_4$, and including any hydrates of the foregoing. In a further embodiment, the copper metal salt is $CuCl_2$ or a hydrate of $CuCl_2$. In another embodiment, the silane-based reducing agent is selected from trietylsilane, trimethylsilane, triisopropylsilane, triphenylsilane, tri-n-propylsilane, tri-n-hexylsilane, triethoxysilane, tris(trimethylsiloxy)silane, tris(trimethylsilyl)silane, di-tert-butylmethylsilane, diethylmethylsilane, diisopropylchlorosilane, dimethylchlorosilane, dimethylethoxysilane, diphenylmethylsilane, ethyldimethylsilane, ethyldichlorosilane, methyldichlorosilane, methyldiethoxysilane, octadecyldimethylsilane, phenyldimethylsilane, phenylmethylchlorosilane, 1,1,4,4-tetramethyl-1,4-disilabutane, trichlorosilane, dimethylsilane, di-tert-butylsilane, dichlorosilane, diethylsilane, diphenylsilane, phenylmethylsilane, n-hexylsilane, n-octadecylsilane, n-octylsilane, and phenylsilane. In a further embodiment, the silane-based reducing agent is tris(trimethylsilyl)silane or triphenylsilane. In yet another embodiment, the surface ligand is selected from oleylamine, trioctylphosphine oxide, oleic acid, 1,2-hexadecanediol, trioctylphosphine, or any combination of the foregoing. In a particular embodiment the surface ligand is oleylamine. In another embodiment, the reaction mixture is heated and maintained at a temperature between about 50° C. to 250° C. In a further embodiment, the reaction mixture is heated and maintained from 160° C. to 200° C. for at least 8 hours. In another embodiment, the ultrathin copper nanowires are collected by centrifugation or filtration. In yet another embodiment, the method further comprises: washing and centrifuging the collected copper elongated nanostructure with a nonpolar organic solvent for a plurality of times. In a particular embodiment, the nonpolar organic solvent comprises hexane.

The disclosure also provides an ultrathin copper elongated nanostructure produced by the method as described above characterized by having a diameter less than 65 nanometers with an aspect ratio greater than 1, and a face-centered cubic structure. In one embodiment, the nanostructure has a diameter between 15 to 25 nanometers. In another embodiment, the nanostructure further comprises a surface copper oxide layer having a thickness up to 2 nm. In still another embodiment, the copper nanostructure is at least 100 nm in length.

The disclosure further provides a transparent electrode conducting material comprising the copper nanostructure disclosed herein, or a film made from copper nanostructures of the disclosure.

The disclosure also provides an optoelectronic device comprising the transparent electrode conducting material described herein. Examples of optoelectronic devices include, but are not limited to, a LCD display, a LED display, a photovoltaic device, a touch panel, a solar panel, a light emitting diode (LED), an organic light emitting diode (OLED), an OLED display, and an electrochromic window.

The disclosure further provides a method to synthesize a metal elongated nanostructure, comprising: forming a reaction mixture comprising a silane-based reducing agent, a metal salt and a surface ligand, wherein the surface ligand may also be a solvent; and maintaining the reaction mixture at ambient temperature or at an elevated temperature between 1 to 48 hours with or without stirring, wherein the metal nanowire comprises silver, aluminum, zinc, nickel, or platinum, and wherein the metal nanostructure has a diameter less than 65 nm and an aspect ratio greater than 1. In one embodiment, the surface ligand is oleylamine. In a further embodiment, the metal nanostructure is collected by centrifugation and/or filtration.

In a particular embodiment, the disclosure also provides for a metal elongated nanostructure made by any of the methods described herein.

In a certain embodiment, the disclosure provides for a transparent electrode comprising a metal elongated nanostructure described herein.

In another embodiment, the disclosure also provides for an optoelectronic device comprising a transparent electrode described herein. Examples of optoelectronic devices include, but are not limited to, a LCD display, a LED display, a photovoltaic device, a touch panel, a solar panel, a light emitting diode (LED), an organic light emitting diode (OLED), an OLED display, and a electrochromic window.

In a certain embodiment, the disclosure further provides for a method to produce a conducting film of annealed metal nanostructures, comprising: (A) forming a network of nanostructures of any one of claims 13 to 16, and 22 on a substrate; and (B) annealing the network of nanostructures at a temperature between 150° C. to 260° C. In a further embodiment, the network of nanowires is formed on a substrate by: filtering down a dispersion of nanostructures onto a polytetrafluoroethylene porous membrane to form a network of nanostructures; and transferring the network of nanostructures from the membrane to a substrate by applying pressure to backside of the membrane and forcing intimate contact between the network of nanostructures to the substrate. In a certain embodiment, the substrate is glass. In a further embodiment, the network of nanostructures are annealed under an atmosphere comprising argon and hydrogen.

In a particular embodiment, the disclosure provides for a conducting film produced by a method disclosed herein.

In a certain embodiment, the disclosure provides for a transparent electrode comprising a conducting film described herein.

In another embodiment, the disclosure also provides for an optoelectronic device comprising a transparent electrode described herein. Examples of optoelectronic devices include, but are not limited to, a LCD display, a LED display, a photovoltaic device, a touch panel, a solar panel, a light emitting diode (LED), an organic light emitting diode (OLED), an OLED display, and a electrochromic window.

DETAILED DESCRIPTION

As used herein and in the appended claims, the singular forms "a," "an," and "the" include plural referents unless the context clearly dictates otherwise. Thus, for example, reference to "a nanowire" includes a plurality of such materials and reference to "the copper oxide layer" includes reference to one or more copper oxides and equivalents thereof known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is recited (e.g., 1 to 70 nm) any value in that range is specifically contemplated by the disclosure (e.g., 2, 3, 4, 5, . . . etc).

Within this description, the terms "nanowires," "nanorods," "nanowhiskers," and "nanopillars" and other similar terms may be used synonymously, except as otherwise indicated. Generally, these terms refer to elongate structures which have lengths and widths, where the length is defined by the longest axis of the structure and the width is defined by the axis generally normal to the longest axis of the structures, and wherein the elongate nanostructures have an aspect ratio greater than one (i.e., length>width in the ratio of length:width). For purposes of this disclosure width and diameter are used synonymously, except as otherwise indicated.

Current technologies for making transparent conductors using indium tin oxide (ITO) provide a good tradeoff between optical transparency and electrical sheet resistance. However, ITO suffers from several drawbacks: (i) indium is becoming a scarce and expensive resource; (ii) sputtering and patterning (lithography) are costly; (iii) ITO films are brittle and inflexible due to poor mechanical ductility; and (iv) ITO films are not transparent in IR region (for PV and windows). Due to these drawbacks, ongoing research and development efforts have been aimed at finding next-generation transparent conducting electrode materials. Among various alternative materials, metal nanowires are an excellent choice because they are solution processable and patternable at low cost. Moreover, metal nanowires are highly flexible, and transparent throughout the wavelength spectrum. Ideally, the metal nanowires have to be very thin (<100 nm) to keep light scattering (haze) at a minimum, but not too thin to sacrifice conductivity. However, state-of-the-art solution-based synthesis approaches described in the art typically afford metal nanowires having diameters in the range of 50-100 nm. By contrast, the disclosure provides innovative synthetic approaches which overcome the limitations of conventional techniques for producing ultrathin metal elongated structures (e.g., structures which are 65 nm or less in diameter).

In various embodiments, the diameter of, for example, a "rod" or "wire" is about 1-70 nm, about 1.2-60 nm, about 1.3-50 nm, about 1.5-40 nm, about 2-30 nm, about 2.5-25 nm, about 3-23 nm, about 10-22 nm, about 17 to 21 nm, about 1-10 nm, about 1-5 nm, about 1 nm, about 1.5 nm, about 2 nm, about 2.5 nm, about 3 nm, about 3.5 nm, about 4 nm, about 4.5 nm, about 5 nm, about 10 nm, about 15 nm, about 16 nm, about 17 nm, about 18 nm, about 19 nm, about 20 nm, about 21 nm, about 22 nm, about 23 nm, about 24 nm, about 25 nm, about 30 nm, about 35 nm, about 40 nm, about 50 nm, or about 60 nm. The diameter for a Cu-nanowire of the disclosure will typically be about 15-25 nm, about 18 nm, about 19 nm, about 20 nm, about 21 nm, or about 22 nm. The length of the "rod" or "wire" is about 50-100 nm, about 80-500 nm, about 100 nm to 1 µm, about 200 nm to 2 µm, about 300 nm to 3 µm, about 400 nm to 4 µm, about 500 nm to 5 µm, about 600 nm to 6 µm, about 700 nm to 7 µm, about 800 nm to 8 µm, about 900 nm to 9 µm, about 1 µm to 10 µm, about 2 µm to 15 µm, about 3 µm to 20 µm, or about 5 µm to 50 µm. For a metal elongated nanostructure (e.g., a Cu-nanowire) disclosed herein, the length will typically be at least 50 nm, at least 60 nm, at least 70 nm, at least 80 nm, at least 90 nm, at least 100 nm, at least 200 nm, at least 500 nm, at least 1 µm, at least 5 µm, at least 10 µm, or at least 15 µm.

The term "aspect ratio" as used herein refers to the ratio of a structure's length to its width. Hence, the aspect ratios of the elongated structures of the disclosure will be greater than one (i.e., length>diameter). In a particular embodiment the aspect ratio, for example, a "rod" or "wire" is greater than 1, greater than 10, greater than 100, greater than 200, greater than 300, greater than 400, greater than 500, greater than 600, greater than 700, greater than 800, greater than 900, greater than 1,000, greater than 1,500, greater than 2,000, or greater than 5,000. The aspect ratio for a Cu-nanowire of the disclosure will typically be greater than 100, greater than 200, greater than 300, greater than 400, greater than 500, greater than 600, or greater than 700.

The methods disclosed herein allows for the production of high-quality metal elongated structures with diameters less than 1 µm. In a particular embodiment, the metal elongated structures have diameters less than 65 nm. Metal elongated structures which comprise diameters in low nanometer range (e.g., <65 nm) generate only a small scattering effect in transparent conductor applications. The metal nanostructures produced by the methods disclosed herein can be comprised of relatively inexpensive material. For example, the nanowires can be comprised of copper, which is one of the most earth-abundant metal elements (10 Abundance, atoms of element per $10^6$ atoms of silicon). By contrast, other conducting metals, like indium ($10^{-2}$ Abundance), silver ($10^{-2}$ Abundance) and gold ($10^{-3}$ Abundance) are much more expensive and rare. In a certain embodiment, methods to produce metal nanostructures disclosed herein are solution-based which is readily scalable and does not require a specially designed reaction chambers with ultra-high vacuum, temperature or delicate plasma control. Moreover, the methods disclosed herein can easily be adapted to allow for size control and controlled growth of a variety of metal-based nanostructures other than copper. For example, silver, gold, aluminum, zinc, nickel, and platinum-based nanostructures can all be synthesized using the methods of the disclosure. Additionally, the methods disclosed herein can also allow for the controlled growth of a variety of semiconductor-based nanostructures, including nanostructures comprising silicon, germanium or tin.

In a particular embodiment, the disclosure provides for a method which comprises forming a reaction mixture. In a further embodiment, the reaction mixture comprises a metal containing precursor compound, typically a metal containing salt. Any number of metal salts are compatible with the methods disclosed herein, including copper based salts, like $Cu(I)I$, $Cu(I)Br$, $Cu(I)Cl$, $Cu(I)F$, $Cu(I)SCN$, $Cu(II)Cl_2$, $Cu(II)Br_2$, $Cu(II)F_2$, $Cu(II)0H_2$, $Cu(II)$D-gluconate, $Cu(II)MoO_4$, $Cu(II)(NO_3)_2$, $Cu(II)(ClO_4)_2$, $Cu(II)P_2O_7$, $Cu(II)SeO_3$, $Cu(II)SO_4$, $Cu(II)$tartrate, $Cu(II)(BF_4)_2$, $Cu(II)(NH_3)_4SO_4$, and any hydrates of the foregoing; gold based salts, like $Au(I)I$, $Au(I)Cl$, $Au(III)Cl_3$, $HAu(III)Cl_4$, $Au(III)Br_3$, $HAu(III)Br_4$, $Au(III)OH_3$, $K(Au(III)CL_4)$ and any hydrates of the foregoing; silver based salts, like $Ag(I)BrO_3$, $Ag_2(I)CO_3$, $Ag(I)ClO_3$, $Ag(I)Cl$, $Ag_2(I)CrO_4$, $Ag(I)$citrate, $Ag(I)OCN$, $Ag(I)CN$, $Ag(I)$cyclohexanebutyrate, $Ag(I)F$, $Ag(II)F_2$, $Ag(I)$lactate, $Ag(I)NO_3$, $Ag(I)NO_2$, $Ag(I)CLO_4$, $Ag_3(I)PO_4$, $Ag(I)BF_4$, $Ag_2(I)SO_4$, $Ag(I)SCN$, and any hydrates of the foregoing; aluminum based salts, like $AlI_3$, $AlBr_3$, $AlCl_3$, $AlF_3$, $Al(OH)_3$, Al-lactate, $Al(PO_3)_3$, $AlO_4P$, $Al_2(SO_4)_3$, and any hydrates of the foregoing; zinc based salts, like $ZnI_2$, $ZnBr_2$, $ZnCl_2$, $ZnF_2$, $Zn(CN)_2$, $ZnSiF_6$, $ZnC_2O_4$, $Zn(ClO_4)_2$, $Zn_3(PO_4)_2$, $ZnSeO_3$, $ZnSO_4$, $Zn(BF_4)_2$, and any hydrates of the foregoing; nickel based salts, like $NiI_2$, $NiBr_2$, $NiCl_2$, $NiF_2$, $(NH_4)_2Ni(SO_4)_2$, $Ni(OCOCH_3)_2$, $NiCO_3$, $NiSO_4$, $NiC_2O_4$, $Ni(ClO_4)_2$, $Ni(SO_3NH_2)_2$, $K_2Ni(H_2IO_6)_2$, $K_2Ni(CN)_4$, and any hydrates of the foregoing; and platinum based salts, like $Pt(II)Br_2$, $Pt(II)Cl_2$, $Pt(II)(CN)_2$, $Pt(II)I_2$, $Pt(II)(NH_3)_2Cl_2$, $Pt(IV)Cl_4$, $H_2Pt(IV)(OH)_6$, $H_2Pt(IV)Br_6$, $Pt(IV)(NH_3)_2CL_4$, and including any hydrates of the foregoing, (wherein (I) indicates a +1 oxidation state, (II) indicates a +2 oxidation state, (III) indicates a +3 oxidation state, and (IV) indicates a +4 oxidation state, respectively, for the metal ion).

In a particular embodiment, a reaction mixture used with the methods disclosed herein comprises a reducing agent. In a further embodiment, the reaction mixture comprises a silane-based reducing agent. Examples of silane-based reducing agents include, but are not limited to, trietylsilane, trimethylsilane, triisopropylsilane, triphenylsilane, tri-n-propylsilane, tri-n-hexylsilane, triethoxysilane, tris(trimethylsiloxy)silane, tris(trimethylsilyl)silane, di-tert-butylmethylsilane, diethylmethylsilane, diisopropylchlorosilane, dimethylchlorosilane, dimethylethoxysilane, diphenylmethylsilane, ethyldimethylsilane, ethyldichlorosilane, methyldichlorosilane, methyldiethoxysilane, octadecyldimethylsilane, phenyldimethylsilane, phenylmethylchlorosilane, 1,1,4,4-tetramethyl-1,4-disilabutane, trichlorosilane, dimethylsilane, di-tert-butylsilane, dichlorosilane, diethylsilane, diphenylsilane, phenylmethylsilane, n-hexylsilane, n-octadecylsilane, n-octylsilane, and phenylsilane. In yet a further embodiment, the methods disclosed herein utilizes a metal containing precursor compound and silane-based reducing agent at a defined molar ratio. For example, the molar ratio between the metal containing precursor compound to silane-based reducing agent is in the range of 1:100 to 100:1, 1:50 to 50:1, 1:30 to 30:1, 1:20 to 20:1, 1:10 to 10:1, 1:5 to 5:1, 1:4 to 4:1, 1:3 to 3:1, 1:2 to 2:1, 2:3 to 3:2, or about 1:1.

In a further embodiment, a reaction mixture used with the methods disclosed herein comprises surface ligand(s). Surface ligands allow for the selective control of the morphology and size of the resulting metal nanowire products. In another embodiment, the surface ligand also functions as a solvent for the synthesis reaction. Examples of surface ligands include, but are not limited to, oleylamine, trioctylphosphine oxide (TOPO), oleic acid, 1,2-hexadecanediol, trioctylphosphine (TOP), or any combination of the foregoing. Alternatively, the methods disclosed herein can comprise a surface ligand and one or more organic nonpolar solvents. Examples of organic nonpolar solvents include, but are not limited to, hexanes, toluene, benzene, pentane, cyclopentane, cyclohexane, 1,4-dioxane, chloroform, diethyl ether, or a mixture of any of the foregoing.

The structural properties, such as diameter, length and shape, of the metal nanostructures of the disclosure can be varied by modifying the reaction conditions, such as the temperature at which the reaction takes place, the amount of starting metal precursor compound, choice of silane based reducing agent, additional solvents, etc. For example, it was found that by slowly heating and maintaining a reaction mixture at 160° C. generated Cu-nanowires that had diameters of 19±2 with an aspect ratio greater than one. By changing the reaction temperature, it could be expected that the diameters of the resulting Cu-nanowire may also change. Accordingly, the methods disclosed herein can be run at room temperature or at an elevated temperature, wherein the heating may be performed with a controlled ramp (e.g., 0.5° C., 1° C., 1.5° C., 2° C., 2.5° C., 3° C., 4° C., or 5° C. per minute). In a particular embodiment, the methods of the disclosure are performed at a temperature between about 20° C. to 360° C., about 30° C. to 300° C., about 50° C. to 250° C., about 80° C. to 220° C., about 100° C. to 200° C., about 120° C. to 180° C., or about 140° C. to 170° C. In another embodiment, the methods disclosed herein may be maintained at a set temperature or at various temperatures for a suitable period of time to allow for product formation. For example, depending upon the identity and/or concentration of starting materials, the reaction temperature, etc. the reactions may be maintained at temperature for as little as a few minutes to more than 24 hours. In a particular embodiment, the reaction may be maintained at a temperature(s) for at least 30 minutes, at least 1 hour, at least 2 hours, at least 3 hours, at least 4 hours, at least 5 hours, at least 6 hours, at least 7 hours, at least 8 hours, at least 9 hours, at least 10 hours, at least 12 hours, at least 16 hours, or at least 24 hours. In an alternate embodiment, the reaction may be maintained at a temperature(s) between 1 to 48 hours, between 1 to 24 hours, between 3 to 12 hours, between 4 to 9 hours, between 5 to 8 hours; or about 5 hours, about 6 hours, about 7 hours, about 8 hours, about 9 hours, about 10 hours, or about 12 hours.

Figure 4A:
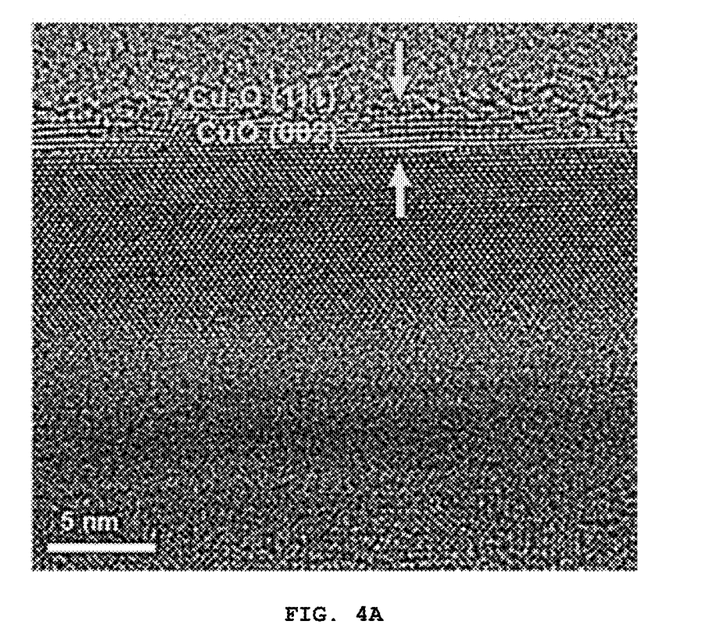
FIG. 4A-B presents HRTEM images of the surface of the Cu nanowire after exposure in air for (A) 2 hours and (B) 5 days.
Figure 4B:
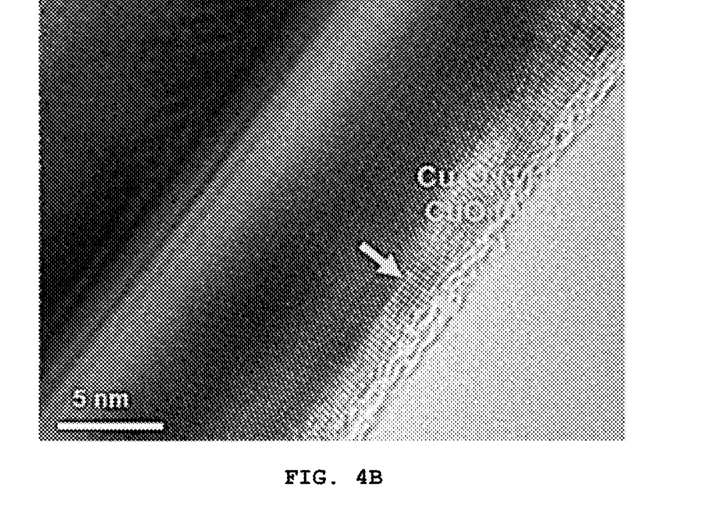

As further shown herein, the metal nanowires of the disclosure have good resistance to environmental oxidation. For example, the as-synthesized copper nanowires disclosed herein quickly formed a surface oxide layer with the thickness about 2 nm (see FIG. 4A). The native copper oxides consist of either CuO or $Cu_2O$ as indicated. The initial surface oxide layer was stable after formation, as indicated by no further oxidation being observed after air exposure for 5 days (see FIG. 4B).

In certain embodiments, the disclosure also provides for fabricating a conducting nanowire network film comprising the metal nanostructures disclosed herein. The metal nanostructures are diluted in a solvent and ultrasonicated to generate a homogenous suspension. The suspension is then dispersed onto a nonabsorbent porous membrane (e.g., a polytetrafluoroethylene membrane) using vacuum filtration. The resulting metal nanostructured network can then be transferred to a substrate, e.g., glass, an annealed at an elevated temperature (e.g., 100° C. to 260° C.). In a particular embodiment, the metal nanostructured network is annealed at around 200° C. In a further embodiment, the metal nanostructured network can be annealed under a reducing atmosphere (e.g., 10% Hydrogen gas in argon) at an elevated temperature (e.g., 100° C. to 260° C.) in order to improve the junction contact of the annealed metal nanostructures. In alternate embodiments, other chemical agents could also be used to the improve the junction contact of the annealed metal nanostructures, such as the use of hydrazine, lithium naphthalenide, sodium naphthalenide, potassium naphthalenide, thiourea dioxide, $NaHSO_3$, sodium borohydride, lithium aluminum hydride, thiophene, and/or ascorbic acid. The resulting annealed metal nanowire network films show great transparency from ultraviolet-visible range to infrared (350-1700 nm), and exhibit outstanding performance in the trade-off between transparency and resistance.

The disclosure further provides a conducting electrode comprising the conducting nanowire network film disclosed herein. In a further embodiment, the conducting electrode is a transparent conducting electrode. The conducting electrodes comprising the metal nanostructured films disclosed herein are ideally suited not only for displays in consumer electronics but also for photovoltaic cells or thermal applications, where transmission in the near-infrared region is also important. In yet a further embodiment, the conducting electrode is used in optoelectronic devices, such as displays (e.g., LCD, LED and OLED), light sources (e.g., LED diodes and OLED diodes), photovoltaic devices, touch panels, and electrochromic windows. In a particular embodiment, solar cells and/or photodetectors comprise a conducting electrode disclosed herein.

The following examples are intended to illustrate but not limit the disclosure. While they are typical of those that might be used, other procedures known to those skilled in the art may alternatively be used.

EXAMPLES

Synthesis of copper nanowires using tris(trimethylsily) silane. $CuCl_2$ (85 mg; 0.5 mmol) and oleylamine (5 g) were mixed in a reaction vessel. The mixture was sonicated at ambient temperature until it became a clear blue solution. Upon addition of tris(trimethylsily)silane (0.5 g; 2 mmol) as reducing regent, the reactor was slowly heated up to 160° C. (2° C./min). The reaction was maintained at 160° C. for 8 hours under stirring. The color of the solution turned light orange and further into reddish brown, indicating formation of copper nanowires. The product was harvested by centrifugation at 6000 rpm for 5 minutes. The nanowires were then washed repeatedly with hexanes by using centrifugation-redispersion cycles to remove excess oleylamine for further characterizations.

Figure 1A:
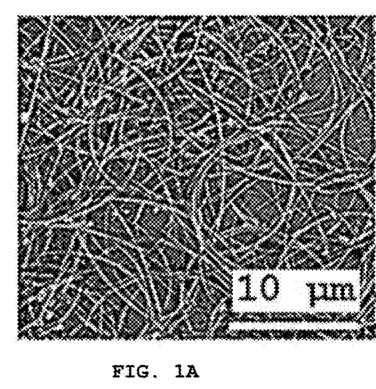
FIG. 1A-E presents electron microscope images and x-ray spectroscopy patterns for the Cu-nanowires of the disclosure. (A) and (B), Scanning Electron Microscopy (SEM) images of the Cu-nanowires. (C) Transmission Electron Microscopy (TEM) images of as-grown Cu-nanowires. (D) Energy-dispersive X-ray spectroscopy (EDS) spectrum of the Cu-nanowires. (E) X-ray diffraction (XRD) pattern of the Cu-nanowires.
Figure 1B:
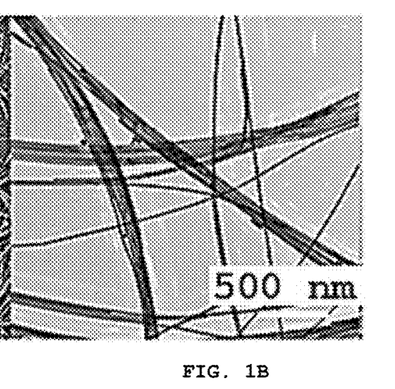
Figure 1C:
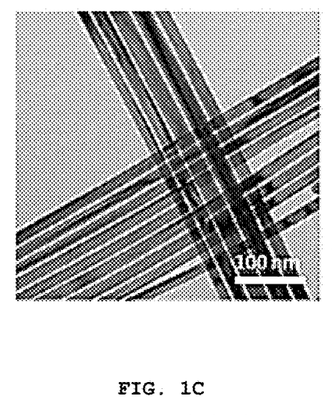
Figure 1D:
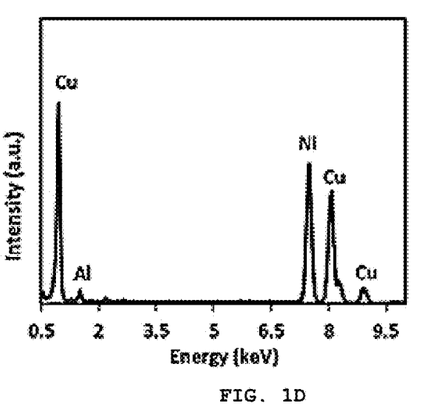
Figure 1E:
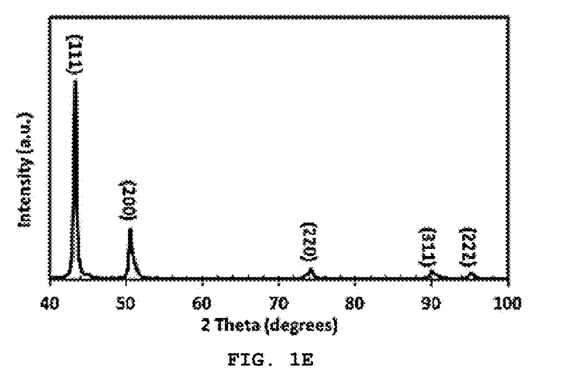

Characterizing the morphologies of the copper nanowires made using tris(trimethylsily)silane. The morphologies of the products were examined by both scanning electron microscopy and transmission electron microscopy (SEM, JOEL JSM-6340F and TEM, Hitachi H7650). As shown in FIG. 1A-C, the product mainly consists of uniform nanowires with minimum portion of nanoparticles. Such uniform nanowires have length of up to 15 μm, and diameter of 19±2 nm. Energy dispersive X-ray spectroscopy (EDAX GENESIS 2000) characterization was also conducted on the as-grown sample to study the composition of the nanowires. The EDS spectrum in FIG. 1D confirms the formation of copper nanowires. The nickel and aluminum signal detected are from TEM grid and sample holder respectively. The XRD spectrum (Bruker D8 Advance) shown in FIG. 1E indicates that copper nanowires have face-centered cubic structure.

Synthesis of copper nanowires using triphenylsilane. $CuCl_2$ (85 mg; 0.5 mmol), triphenylsilane(0.52 g; 2 mmol) and oleylamine (5 g) were mixed in a reaction vessel. The mixture was sonicated at ambient temperature until it became a clear blue solution. Then, the reactor was slowly heated up to 200° C. (2° C./min). The reaction was maintained at 200° C. for 8 hours under stirring. The color of the solution turned light orange and further into reddish brown, indicating formation of copper nanowires. The product was harvested by centrifugation at 8000 rpm for 15 minutes. The nanowires were then washed repeatedly with hexanes by using centrifugation-redispersion cycles to remove excess oleylamine for further characterizations.

Figure 2A:
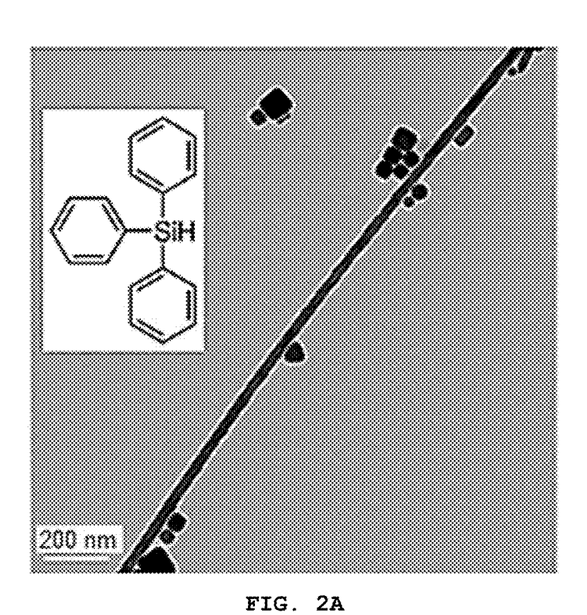
FIG. 2A-B presents electron microscope images of as-grown Cu-nanowires using triphenylsilane. (A) As-synthesized copper wires (Inset: triphenylsilane); and (B) Higher magnification of the as-synthesized copper nanowires.
Figure 2B:
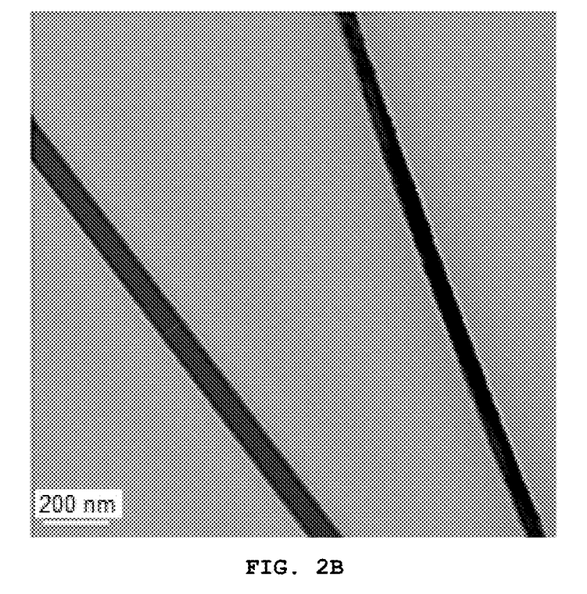

Characterizing the morphologies of the copper nanowires made using triphenylsilane. The morphologies of the products were examined by electron microscopy. The products were found to be mainly uniform nanowires with minimum portion of nanoparticles (e.g., see FIG. 2A). The copper nanowires were found to have mean diameter of around 60 nm (e.g., see FIG. 2B).

Figure 3A:
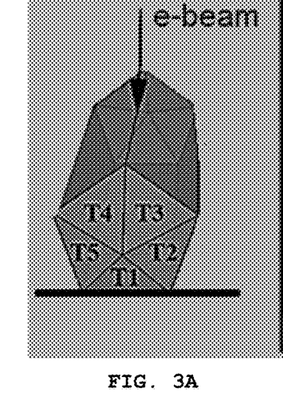
FIG. 3A-F provides schematics of copper nanowire structures consisting of five twinned FCC subunits, where one of the side surfaces is (A-C) perpendicular to the electron beam and (D-F) parallel to the electron beam. (B) and (C) show selected area (electron) diffraction (SAED) patterns and high-resolution transmission electron microscopy (HRTEM) images of the Cu-nanowire corresponding to scenario described in (A). (E) and (F) show SAED patterns and HRTEM images of the Cu-nanowire corresponding to scenario described in (D).
Figure 3B:
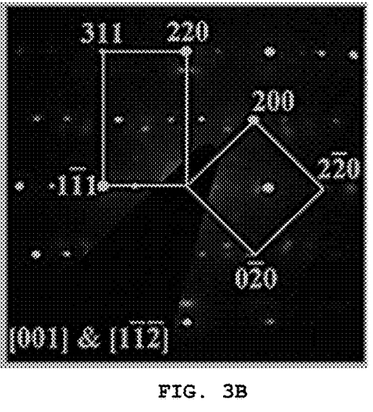
Figure 3C:
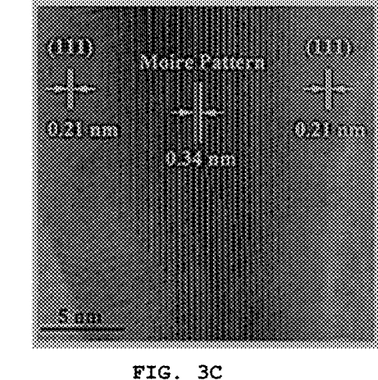
Figure 3D:
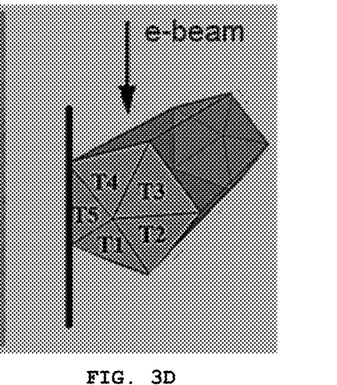
Figure 3E:
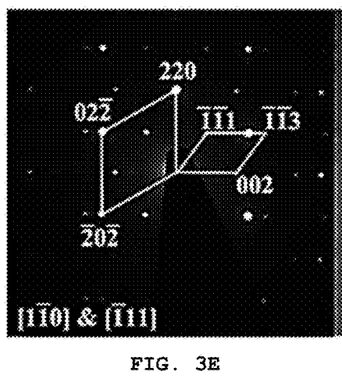
Figure 3F:
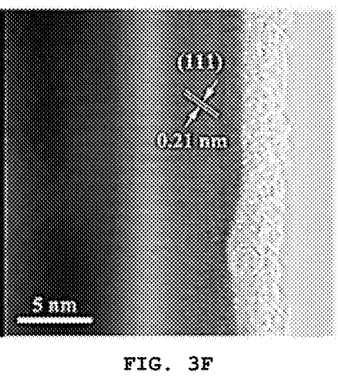

Determining the structural characteristics of the copper nanowires. The structure of the copper nanowires was analyzed using high resolution transmission electron microscopy (HRTEM, FEI Tecnai G20) and selected area electron diffraction (SAED). Cu-nanowires were proved to have five-fold twinned pentagonal structure. FIGS. 3A and D demonstrate the five-fold symmetry of the as-grown Cu nanowire which can be regarded as consisting of five single-crystalline units (T1-5) with face centered cubic (FCC) structure. FIG. 3B-C show the SAED pattern and HRTEM image taken when the electron beam was perpendicular to one of the side face (indicated by red dot line). Two sets of FCC patterns were observed: one with zone axis [001] and the other with [112]. The diffraction pattern with zone axis of [001] direction can be attribute to the crystal sub-lattice of T1 in FIG. 3A while the fringes with [112] zone axis are generated from T3 and T4 sublattice. FIG. 3C also highlights the Moire pattern which is generated from the overlapping of the copper FCC unit cell planes ((111) plane and (220) plane). When the electron beam is directed to be parallel to the side face, as shown in FIG. 3D-F, the FFT corresponds to the overlapping of two FCC pattern with [110] and [111] zone axes. Combining with the above-mentioned characterization where electron beam is perpendicular to side surface, the copper nanowire's five-twinned structure is concluded.

Fabrication of high performance transparent electrode comprising an annealed metal nanostructured film. High-performance copper nanowire electrodes were fabricated on glass using a filtration method. To make a conductive thin film, copper nanowires were diluted using toluene and sonicated for 15 min to form a homogenous suspension. The thin film was constructed by filtering down the nanowires from the dispersion onto a nitrocellose porous membrane (pore size 220 nm) via vacuum filtration. The nanowire network was transferred to a transparent substrate (glass or PET) by applying pressure to the back side of the membrane and forcing an intimate contact with the substrate. The copper nanowire thin film was then annealed under forming gas (10% $H_2$ and 90% Ar) at 200° C. for 30 min to improve junction contact.

Figure 5A:
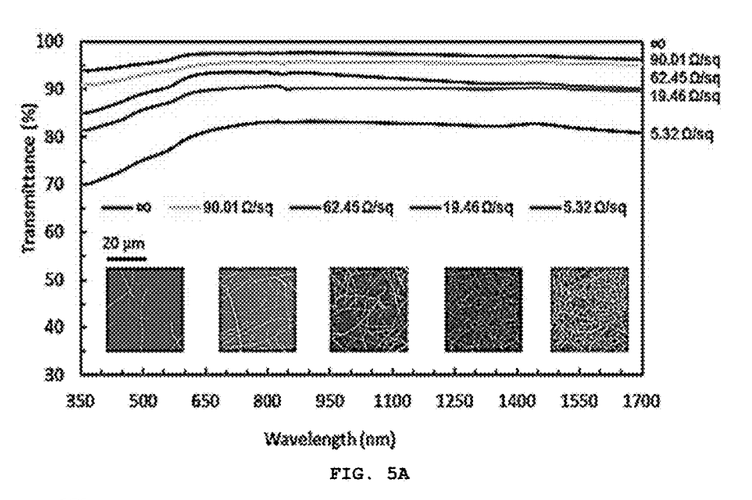
FIG. 5A-B presents physical and electrical characterization of the fabricated transparent films. (A) SEM images, transmittance spectra and measured sheet resistances of the transparent films. (B) Plot of transmittance(%) versus resistance of the transparent films.
Figure 5B:
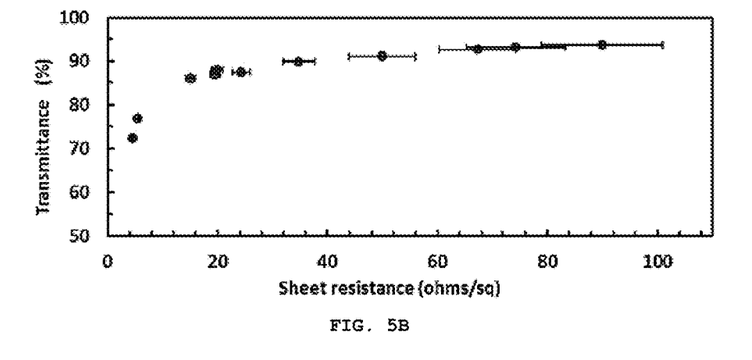

As shown in FIG. 5A, the films show great transparency from ultraviolet-visible range to infrared (350-1700 nm), rendering them suitable materials not only for displays in consumer electronics but also for photovoltaic cells or thermal applications, where transmission in the near-infrared region is also important. Moreover, the conducting films exhibit outstanding performance in the trade-off between transparency and resistance as plotted in FIG. 5B. For a film with transmittance of 77%, the sheet resistance was found to be as low as 5.32 ohms/sq. As the transmittance increased to 86%, the sheet resistance increased only slightly to 15.0 ohms/sq, while another sample showed 90% in transmittance and 34.8 ohms/sq in sheet resistance.

Figure 6A:
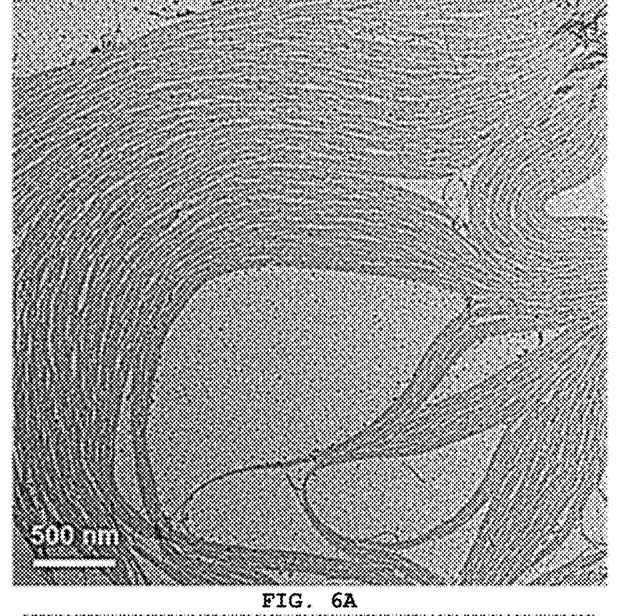
FIG. 6A-B presents TEM images of the surface of Au nanowires synthesized using the methods disclosed herein. (A) Lower magnification of the Au nanowires; and (B) higher magnification of the Au nanowires.
Figure 6B:
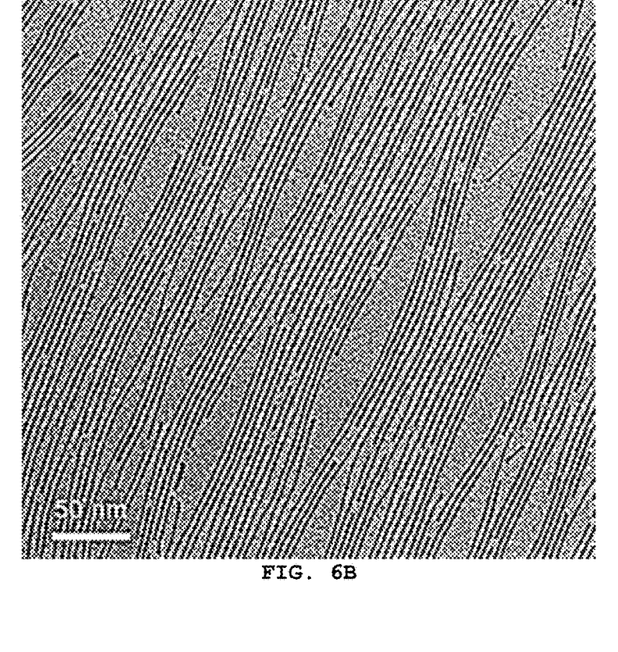

Synthesis of gold nanowires. To synthesize a gold nanowire, $HAuCl_4$ was used as gold source and oleylamine was added as a ligand. Triethylsilane was chosen as the reducing regent instead of tris(trimethylsily)silane given higher activity of gold precursor. After performing the reaction at room temperature for 10 hours, Au nanowires with a mean diameter of 3 nm were obtained (see FIG. 6).

A number of embodiments have been described herein. Nevertheless, it will be understood that various modifications may be made without departing from the spirit and scope of this disclosure. Accordingly, other embodiments are within the scope of the following claims.

What is claimed is:

1. A method to synthesize an ultrathin copper elongated nanostructure having a diameter less than 65 nanometers with an aspect ratio greater than 1, and a face-centered cubic structure, comprising:
   forming a reaction mixture comprising a silane-based reducing agent, a copper metal salt and a surface ligand, wherein the surface ligand may also be a solvent; and
   heating and maintaining the reaction mixture at a temperature from 160° C. to 200° C. between 1 to 48 hours with or without stirring.

2. The method of claim 1, wherein the copper metal salt is selected from CuI, CuBr, CuCl, CuF, CuSCN, $CuCl_2$, $CuBr_2$, $CuF_2$, $CuOH_2$, Cu-D-gluconate, $CuMoO_4$, $Cu(NO_3)_2$, $Cu(ClO_4)_2$, $CuP_2O_7$, $CuSeO_3$, $CuSO_4$, Cu-tartrate, $Cu(BF_4)_2$, $Cu(NH_3)_4SO_4$, and including any hydrates of the foregoing.

3. The method of claim 2, wherein the copper metal salt is $CuCl_2$ or a hydrate of $CuCl_2$.

4. The method of claim 1, wherein the silane-based reducing agent is selected from trietylsilane, trimethylsilane, triisopropylsilane, triphenylsilane, tri-n-propylsilane, tri-n-hexylsilane, triethoxysilane, tris(trimethylsiloxy)silane, tris (trimethylsilyl)silane, di-tert-butylmethylsilane, diethylmethylsilane, diisopropylchlorosilane, dimethylchlorosilane, dimethylethoxysilane, diphenylmethylsilane, ethyldimethylsilane, ethyldichlorosilane, methyldichlorosilane, methyldiethoxysilane, octadecyldimethylsilane, phenyldimethylsilane, phenylmethylchlorosilane, 1,1,4,4-tetramethyl-1,4-disilabutane, trichlorosilane, dimethylsilane, di-tert-butylsilane, dichlorosilane, diethylsilane, diphenylsilane, phenylmethylsilane, n-hexylsilane, n-octadecylsilane, n-octylsilane, and phenylsilane.

5. The method of claim 4, wherein the silane-based reducing agent is tris(trimethylsilyl)silane or triphenylsilane.

6. The method of claim 1, wherein the surface ligand is selected from oleylamine, trioctylphosphine oxide, oleic acid, 1,2-hexadecanediol, trioctylphosphine, or any combination of the foregoing.

7. The method of claim 6, wherein the surface ligand is oleylamine.

8. The method of claim 1, wherein the reaction mixture is slowly heated with ramp of 2° C. /min up to a temperature from 160° C. to 200° C., and maintained at 160° C. to 200° C. for at least 8 hours.

9. The method of claim 1, wherein the ultrathin copper nanowires are collected by centrifugation or filtration.

10. The method of claim 9, wherein the method further comprises:
washing and centrifuging the collected copper elongated nanostructure with a nonpolar organic solvent for a plurality of times.

11. An ultrathin copper elongated nanostructure produced by the method of claim 1.

12. The copper nanostructure of claim 11, wherein the nanostructure has a diameter between 15 to 25 nanometers.

13. The copper nanostructure of claim 11, wherein the nanostructure further comprises a surface copper oxide layer with a thickness up to 2 nm.

14. The copper nanostructure of claim 11, wherein the copper nanostructure is at least 100 nm in length.

15. A transparent electrode conducting material comprising the copper nanostructure of claim 11.

16. An optoelectronic device comprising the transparent electrode material of claim 15.

17. The optoelectronic device of claim 16, wherein the optoelectronic device is selected from the group consisting of a LCD display, a LED display, a photovoltaic device, a touch panel, a solar panel, a light emitting diode (LED), an organic light emitting diode (OLED), an OLED display, and a electrochromic window.

18. A method to synthesize a metal elongated nanostructure, comprising:
forming a reaction mixture comprising a silane-based reducing agent, a metal salt and a surface ligand, wherein the surface ligand may also be a solvent; and
maintaining the reaction mixture at a temperature from 20° C. to 360° C. between 1 to 48 hours with or without stirring;
wherein the metal elongated nanostructure comprises silver, aluminum, zinc, nickel, or platinum, and wherein the metal nanostructure has a diameter less than 65 nm and an aspect ratio greater than 1.

19. The method of claim 18, wherein the surface ligand is oleylamine.

20. The method of claim 18, wherein the metal nanostructure is collected by centrifugation and/or filtration.

21. A metal elongated nanostructure made by the method of claim 18.

22. A transparent electrode comprising the metal elongated nanostructure of claim 21.

23. An optoelectronic device comprising the transparent electrode of claim 22.

24. The optoelectronic device of claim 23, wherein the optoelectronic device is selected from the group consisting of a LCD display, a LED display, a photovoltaic device, a touch panel, a solar panel, a light emitting diode (LED), an organic light emitting diode (OLED), an OLED display, and a electrochromic window.

* * * * *